(12) United States Patent
Nagatani et al.

(10) Patent No.: US 11,726,024 B2
(45) Date of Patent: Aug. 15, 2023

(54) RECYCLED CONCRETE PREPARATION USING SENSORS TO CHARACTERIZE PARTICLES AND CONTROL CARBONATION AND DENSIFICATION PROCESS STEPS

(71) Applicant: X Development LLC, Mountain View, CA (US)

(72) Inventors: Ray Jr. Anthony Nagatani, San Francisco, CA (US); Antonio Raymond Papania-Davis, Oakland, CA (US)

(73) Assignee: X Development LLC, Mountain View, CA (US)

( * ) Notice: Subject to any disclaimer, the term of this patent is extended or adjusted under 35 U.S.C. 154(b) by 0 days.

(21) Appl. No.: 17/934,473

(22) Filed: Sep. 22, 2022

(65) Prior Publication Data

US 2023/0093848 A1 Mar. 30, 2023

Related U.S. Application Data

(60) Provisional application No. 63/248,259, filed on Sep. 24, 2021.

(51) Int. Cl.
*G01N 15/02* (2006.01)
*G01N 33/38* (2006.01)
(Continued)

(52) U.S. Cl.
CPC ....... *G01N 15/1434* (2013.01); *C04B 18/167* (2013.01); *C04B 20/107* (2013.01);
(Continued)

(58) Field of Classification Search
CPC .. G01N 15/0205; G01N 33/383; C04B 14/04; C04B 18/167; C04B 20/023; C04B 20/107
(Continued)

(56) References Cited

U.S. PATENT DOCUMENTS 9,707,513 B2 7/2017 Constantz et al.
9,714,406 B2 7/2017 Constantz et al.
(Continued)

FOREIGN PATENT DOCUMENTS

WO WO 2020/217232 10/2020

OTHER PUBLICATIONS

Engelsen et al., "Carbon dioxide uptake in demolished and crushed concrete," CO2 Uptake During the Concrete Life Cycle Nordic Innovation Centre Project 03018, Project 395, 2005, 38 pages.
(Continued)

*Primary Examiner* — Arlen Soderquist
(74) *Attorney, Agent, or Firm* — Fish & Richardson P.C.

(57) ABSTRACT

Methods, systems, and apparatus, including computer programs encoded on computer storage media, for processing recycled concrete aggregate (RCA). One of the methods includes obtaining first optical measurements of RCA particles as the RCA particles are conveyed past the first optical sensors; determining, based on the first measurements, an initial characterization of the RCA particles; iteratively performing a carbonation process on the RCA particles, obtaining second optical measurements of the RCA particles, and determining, from the second measurements, a second characterization of the RCA particles, wherein conditions of the carbonation process are initially set based on the initial characterization, and the conditions of the carbonation process are adjusted based on the second characterization; ceasing the iterative performance of the carbonation process in response to the second characterization meeting target carbonation characteristics; iteratively performing a densification process on the RCA particles, obtaining third optical measurements of the RCA particles, and determining, from the third measurements, a third characterization of the RCA particles, wherein conditions of
(Continued)

the densification process are initially set based on the initial characterization or the second characterization, and the conditions of the densification process are adjusted based on the third characterization; and ceasing the iterative performance of the densification process in response to the third characterization meeting target densification characteristics.

20 Claims, 4 Drawing Sheets

(51) Int. Cl.
    *C04B 18/16*     (2023.01)
    *C04B 20/10*     (2006.01)
    *G01N 15/14*     (2006.01)
    *C04B 18/167*     (2023.01)

(52) U.S. Cl.
    CPC ..... *C04B 20/1074* (2013.01); *G01N 15/0205* (2013.01); *G01N 33/383* (2013.01)

(58) Field of Classification Search
    USPC .................................. 209/10, 552, 570, 586
    See application file for complete search history.

(56) References Cited

U.S. PATENT DOCUMENTS

| | | |
|---|---|---|
| 9,993,799 B2 | 6/2018 | Constantz et al. |
| 10,197,747 B2 | 2/2019 | Constantz et al. |
| 10,203,434 B2 | 2/2019 | Constantz et al. |
| 10,287,439 B2 | 5/2019 | Constantz et al. |
| 10,322,371 B2 | 6/2019 | Constantz et al. |
| 10,711,236 B2 | 7/2020 | Constantz et al. |
| 10,766,015 B2 | 9/2020 | Constantz et al. |
| 10,898,854 B2 | 1/2021 | Constantz et al. |
| 10,960,350 B2 | 3/2021 | Constantz et al. |
| 11,181,700 B2 | 11/2021 | Constantz et al. |
| 11,262,488 B2 | 3/2022 | Constantz et al. |
| 11,344,861 B2 | 5/2022 | Constantz et al. |
| 2017/0226021 A1* | 8/2017 | Sant ........................ C04B 28/10 |
| 2017/0274318 A1* | 9/2017 | Constantz .............. B01D 53/96 |
| 2017/0283293 A1* | 10/2017 | Shin ........................ C04B 14/28 |
| 2020/0129916 A1* | 4/2020 | Constantz .......... B01D 53/1475 |
| 2020/0290924 A1* | 9/2020 | Kicklighter ............. F27B 1/005 |
| 2020/0370001 A1 | 11/2020 | Constantz et al. |
| 2021/0162340 A1 | 6/2021 | Constantz et al. |
| 2021/0236989 A1 | 8/2021 | Constantz et al. |
| 2021/0356680 A1 | 11/2021 | Constantz et al. |
| 2022/0002203 A1* | 1/2022 | Clarens ................. C04B 22/062 |
| 2022/0013196 A1* | 1/2022 | Monkman .............. G06Q 50/08 |
| 2022/0194852 A1* | 6/2022 | Thomas .................. C04B 18/16 |
| 2022/0214477 A1 | 7/2022 | Constantz et al. |
| 2022/0250028 A1 | 8/2022 | Constantz et al. |

OTHER PUBLICATIONS

International Search Report and Written Opinion in International Appln. No. PCT/US2022/044254, dated Jan. 19, 2023, 14 pages.
Lo et al., "Curing effects on carbonation of concrete using a phenolphthalein indicator and Fourier-transform infrared spectroscopy," Building and Environment, May 1, 2002, 37(5):507-514.
Sereng et al., "Improvement of Recycled Aggregates Properties by Means of CO2 Uptake," Applied Sciences, 2021, 11:6571.
Shaban et al., "Properties of recycled concrete aggregates strengthened by different types of pozzolan slurry," Construction and Building Materials, Aug. 1, 2019, 216:632-647.

* cited by examiner

RECYCLED CONCRETE PREPARATION USING SENSORS TO CHARACTERIZE PARTICLES AND CONTROL CARBONATION AND DENSIFICATION PROCESS STEPS

CROSS-REFERENCE TO RELATED APPLICATION

This application claims the benefit of the filing date of U.S. Provisional Application No. 63/248,259, filed on Sep. 24, 2021. The contents of U.S. Application No. 63/248,259 are incorporated herein by reference in their entirety

BACKGROUND

Concrete is the second most consumed substance (by mass) on our planet and is responsible for 7-8% of global CO2 emissions. Concrete's material properties are inconsistent due to the large variation in ingredient material (e.g., aggregates) and processing. This material inconsistency requires large safety margins for a given performance level and results in material overuse. Advances in concrete preparation that can optimize the use of locally available materials to maximize concrete performance while minimizing cost with both traditional and non-traditional concrete ingredients are desirable.

Projections for growth in global construction over the next decade are quite robust. This growth will compound an existing problem: over 6 billion tons of construction and demolition waste are generated by this activity, and most of it goes to landfill. In addition to the environmental consequences stemming from overfilling of landfills, there are also economic consequences as landfill costs can be substantial in several high growth markets. This represents an equally large waste of material and energy that could significantly lower the environmental and dollar cost of producing new materials for construction.

Additionally, global $CO_2$ levels may continue to rise because of this increased level of construction. However, processes for capturing and sequestering carbon are quite costly, making it challenging to offset the $CO_2$ impact of construction while maintaining budget feasibility.

SUMMARY

In general, this disclosure relates to a process and system for preparing and mixing recycled concrete to achieve target post-curing characteristics. In particular, a system is disclosed that assesses the geometric and chemical makeup of particles and upgrades properties of the particles. The properties can be upgraded using a process that includes carbonation, densification, or both. Both carbonation and densification can be performed by matching an amount of reactive cement components within the concrete waste to additives to maximize the interaction and create enhanced aggregate characteristics. The system can also assess output characteristics (e.g., geometry, compressive strength) to iteratively optimize upstream processes (e.g., carbonation, densification, output size/geometry after crush) and continuously refine output particles characteristics to meet application requirements.

A large portion of construction and demolition waste is concrete. While some portion of concrete waste is crushed and recycled into new concrete as recycled concrete aggregate (RCA), it is a small fraction of the total waste in some markets and it is generally only suitable for lower performance applications such as road filler. For high performance or structural applications, virgin quarried aggregate is preferred as recycled concrete can have detrimental effects on the performance. Older concrete recipes may have created low compression strength concrete for low-strength requirement applications. Additionally, as the older concrete is a waste product, it may have been weakened due to environmental exposure during its lifetime or during the demolition process.

Concrete waste has the potential for $CO_2$ uptake. Uptake rates are highly dependent on input composition (e.g., size/surface area, chemical composition) and treatment regimes. Therefore, If the majority of concrete waste is to be recycled for broader replacement of virgin aggregate and to sequester $CO_2$, the process must be able to characterize in real time the changing geometric and chemical characteristics of waste material inputs and adapt downstream processes and recommendations in real-time. Additionally, the strength and durability characteristics of older, lower-quality concrete aggregate waste must be augmented to prevent limitation of the performance. Furthermore, output treated particles must be characterized in real time to determine whether treatment was sufficient to meet specification (e.g., compressive strength), and whether upstream treatment processes (e.g., crush, $CO_2$ uptake, chemical treatment) are enabling the desired outcome.

The disclosed techniques use rapid characterization of heterogeneous and dynamic inputs to holistically treat input concrete waste particles to improve characteristics to meet high performance specifications.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
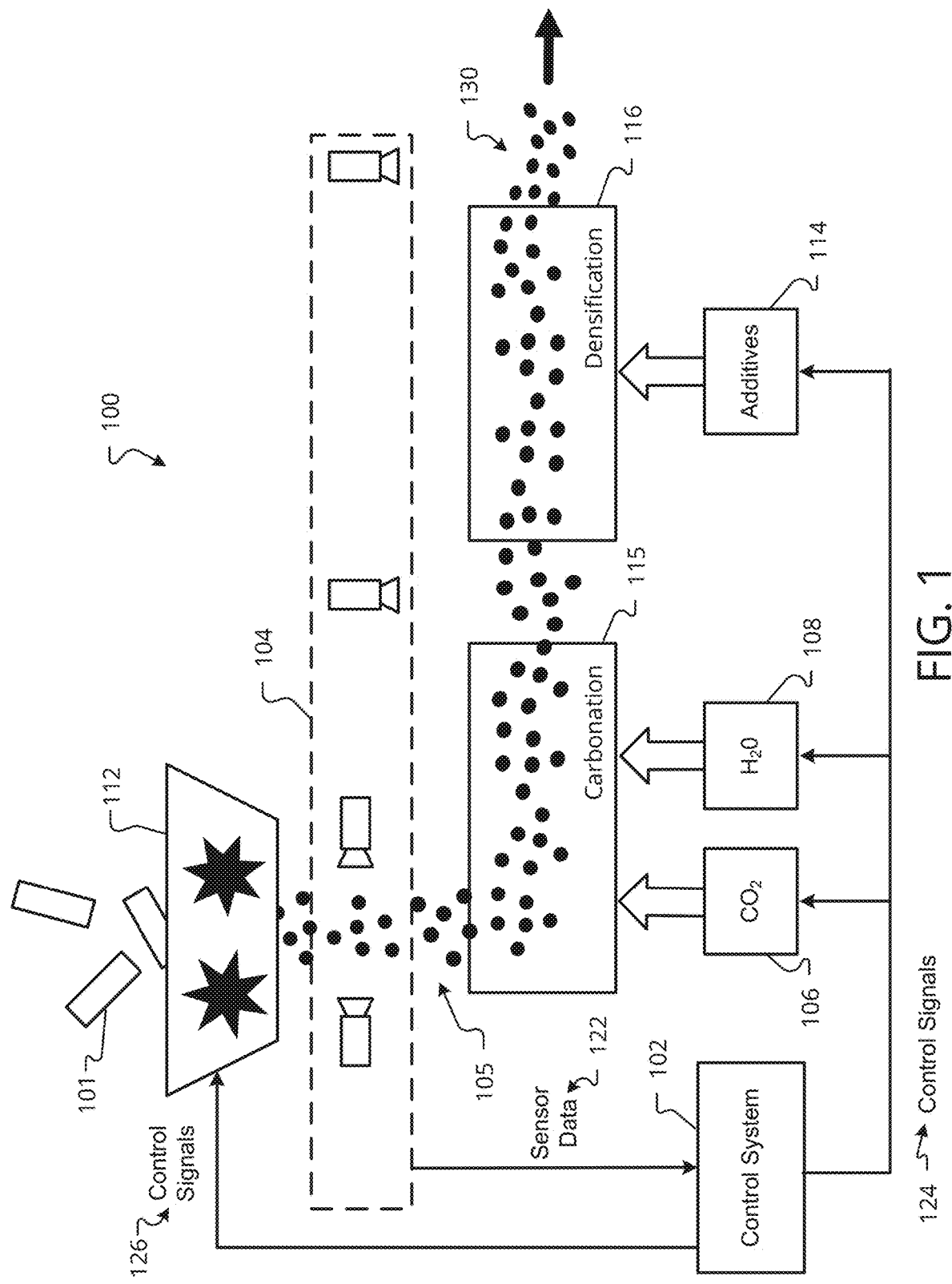
FIG. 1 depicts an exemplary recycled concrete preparation system.

FIG. 1 depicts an exemplary recycled concrete preparation system 100. In operation, the recycled concrete preparation system 100 crushes concrete waste 101 in a crusher 112. The crusher 112 can crush the concrete waste 101 to particular sizes and/or geometries. Operations of the crusher 112 can be controlled by control signals 126 from a control system 102. For example, control signals 126 from the control system 102 can cause the crusher 112 to increase or decrease sizes of crushed concrete particles 105. Particle analysis sensors 104 measure characteristics of the crushed concrete particles 105. Recycled concrete preparation system 100 can upgrade the particles and achieve desired structural properties by adaptively adjusting the proportion of $CO_2$ 106, $H_2O$ 108, and additives 114 added to the particles 105 based on the measured characteristics. The operation of the system 100 is described in more detail below in reference to FIGS. 2 and 3.

Recycled concrete preparation system 100 includes the control system 102. The control system 102 receives input from sensors 104. The control system 102 can control the operations of one or more ingredient metering systems based on analyses of data obtained from the sensors 104.

Crushed particles 105 can be conveyed from the crusher 112 to a carbonation system 115 and to a densification system 116. For example, the particles 105 can be conveyed by a series of conveyors and augers. The particles 105 are passed through the sensors 104 prior to delivery to the carbonation system 115, in between the carbonation system 115, and after departing from the densification system 116. In some examples, the particles 105 can pass through the densification system 116 prior to passing through the carbonation system 115. In some examples, the particles 105 might pass through only one of the carbonation system 115 or the densification system 116.

The sensors 104 are arranged to obtain measurement data of concrete particles. For example, in some implementations optical sensors can be arranged in an array along a conveyor or a chute used to convey the particles to the carbonation system 115. The optical sensors can transmit images of the particles to the control system 102, which (as explained in more detail below) can use image processing algorithms to identify particle shapes and sizes.

Some implementations can include a series of sieves to separate particles by size. In such implementations, the optical sensors can be positioned proximate to each sieve to capture images of the particles passing through the sieve. The images can then be used, for example, to determine an approximate count of each size range of particles exiting each sieve. In such implementations, the separated particles may be recombined before being provided to the carbonation system 115.

The sensors 104 can include various different sensors configured to measure various characteristics of concrete particles. For example, the sensors used by the sensors 104 can include, but are not limited to, optical sensors (e.g., visible light cameras, infra-red cameras, near IR (NIR) sensors, dynamic optical microscopy sensors) and mechanical sensors (e.g., sieves, sedigraphs, impact hammer, electrodynamic vibrator), and spectrometers. In some examples, diffuse reflectance spectroscopy can be used across the visible, near- and shortwave-infrared spectral regions (400 to 2500 nm) as a tool to assess the strength of particles.

Analysis of the particles can be determined by, but is not limited to, NIR optical sensing and regression models to correlate reactant content with images in samples. In some examples, sensor data from the sensors 104 can be used to create a synthetic digital twin of the particles 105.

The measurement data is used by the control system 102 to determine characteristics of the particles 105. For example, particle characteristics can include, but are not limited to, particle sizes, shapes, surface areas, sphericity, porosity, density, strength, and particle size distribution. In some examples, the measurement data can be used to determine exposure of particles to elements such as seawater.

In some implementations, the recycled concrete preparation system may include a metering hopper. The metering hopper can be used to collect and measure (e.g., weigh) particles as they pass through the sensors 104. For example, the weight of the particles measured by metering hopper can be passed to the control system 100 permitting the control system to monitor the weight of the particles being measured in real-time. In some implementations, recycled concrete preparation system 100 can be retro-fit to a traditional ready-mix concrete plant. For example, adding the recycled concrete preparation system 100 to a ready-mix plant may allow the ready-mix plant to more precisely tailor concrete mixes for specific applications and job sites.

The control system 102 can analyze the particles 105 using sensor data 122 from the sensors 104. The particle analysis can be used to optimize the additive reactant and process parameters. For example, the control system 102 can send control signals 124 to control an amount of $CO_2$ and $H_2O$ provided to the particles 105 by the carbonation system 115. The control system 102 can also send control signals 124 to control an amount of additives 114 provided to the particles 105 by the densification system 116. By adaptively maximizing the degree to which additive reactions accrue, carbon uptake by the particles can be increased. Additionally, compression strength of heterogeneous particle mixtures can be enhanced.

The carbonation system 115 performs a process for accelerated carbonation of the particles 105. Based on the size, surface area, shape, porosity, water absorption rate, and calcium hydroxide content of the particles 105, the carbonation system 115 determines suitable process conditions for the accelerated carbonation. The process conditions include, for example, temperature, water vapor, and $CO_2$ concentration.

A purpose of the accelerated carbonation process is to store the largest possible amount of $CO_2$ in the particles in order to improve particle properties. Carbonation decreases the water absorption coefficient by filling pores due to the formation of calcium carbonates. Thus, carbonation leads to the formation of calcium carbonates and to a decrease in total porosity. The capillary porosity is decreased due to clogging of the pores. In addition, carbonation increases the microporosity of particles as a result of decalcification and mercury intrusion.

The densification system 116 performs a densification process. Based on characteristics of the particles after carbonation, the densification system 116 can apply suitable amounts and types of additives 114. The additives 114 can include, for example, silicate sources and catalysts to maximize reactivity. The densification process can improve the quality of particles by using pozzolanic and sodium silicate solution as treatment solutions. Sodium silicate combined with pozzolanic materials can improve mechanical properties of particles. For example, a solution of sodium silicate and silica fume can improve compressive strength of particles.

The densification system 116 produces upgraded particles 130. Upgraded particles 130 can be particles that have undergone a carbonation process, a densification process, or both. A post processing characterization stage can be performed using the same reactivity estimation and other optically determined physical characteristics to provide an accurate qualification of the upgraded particles' compression strength, porosity, uniformity, and other physical characteristics. This measure can allow for quality control by providing insights into material strength, water absorption, and flowability.

In some examples, the sensors 104 can analyze the output treated aggregate, e.g., upgraded particles 130, and can provide feedback to the control system 102. Based on the feedback from the sensors 104, the control system 102 can use control signals 124, 126 to adjust one or more of a size of particles 105 crushed by the crusher 112, an amount of $CO_2$ 106, an amount of $H_2O$ 108, or an amount of additives 114 to improve the characteristics of the upgraded particles 130.

The upgraded particles 130 can be mixed into a concrete mixture. Concrete mix sensors provide rheometry measurements of the concrete mixture to the control system 102. For example, the concrete mix sensors can measure various attributes of the concrete mixture that can be used to estimate or compute rheumatic properties of the concrete mixture in real-time. The concrete mix sensors can include, but are not limited to, viscosity sensors, rheometers, temperature sensors, moisture sensors, ultrasonic sensors (e.g., ultrasonic pulse velocity sensors), electrical property sensors (e.g., electrodes, electrical resistance probes), electromagnetic sensors (e.g., short-pulse radar), or other sensors (e.g., geophone, accelerometer). The concrete mix sensors can include, but are not limited to, hydrophobicity, moisture content, XRD spectra, XRF spectra, static yield stress, acoustic impedance, p-wave speed, dynamic yield stress, static modulus of elasticity, Young's modulus, bulk modulus, shear modulus, dynamic modulus of elasticity (DME), Poisson's ratio, density, resonance frequency, nuclear magnetic resonance (NMR), dielectric constant, electric resistivity, polarization potential, and capacitance.

For example, viscosity, moisture, and temperature sensors can be used to measure rheologic properties of the concrete mixture such as changes in the viscosity of the mixture over time and at different moisture content levels and temperatures. As described in more detail below, the control system 102 can use the rheometry measurements to determine whether and how much additional ingredients and/or additives should be added to the concrete mixture to obtain desired concrete properties.

In some examples, rheometry measurements are performed on an initial concrete mixture made from the upgraded particles 130. Rheometry measurements of the concrete mixture can be estimated based on the measured characteristics of the particles. The rheometry measurements are used to predict characteristics of the concrete after curing. The actual rheometry measurements of the concrete mixture can be obtained and compared with the estimated rheometry to determine whether to adjust an amount of additives. The system can determine, based on the rheometry measurements, whether the concrete mixture is likely to achieve a desired set of post-curing characteristics. If not, the initial mixture is adjusted through an iterative process until the rheometry measurements indicate that the concrete mixture is likely to achieve the desired post-curing characteristics.

During the iterative adjustment process, upgraded particles 130 are incrementally added to the initial concrete mixture while changes in the rheometry measurements are monitored. Additional upgraded particles 130 are added until the rheometry measurements indicate that the concrete mixture is likely to achieve the desired post-curing characteristics. Such post-curing characteristics can include, but are not limited to, compressive strength, tensile/flexural strength, flowability, toughness, cure time, cure profile, finish, density (wet & dry), thermal insulation, shrinkage, and slump.

Post-curing characteristics can be determined from rheometry measurements by, e.g., using multi-dimensional lookup tables relating experimentally obtained post-curing characteristics to mixtures with known rheological properties, by applying theoretical and analytical particle packing model-based Bayesian optimization algorithms to the rheometry measurements, or a combination thereof.

In some examples, the post-curing characteristics can be provided as feedback to the control system 102. Based on the feedback, the control system 102 can use control signals 124, 126 to adjust one or more of a size of particles 105 crushed by the crusher 112, an amount of CO2 106, an amount of $H_2O$ 108, or an amount of additives 114 to improve the characteristics of the cured concrete mixture.

Figure 2:
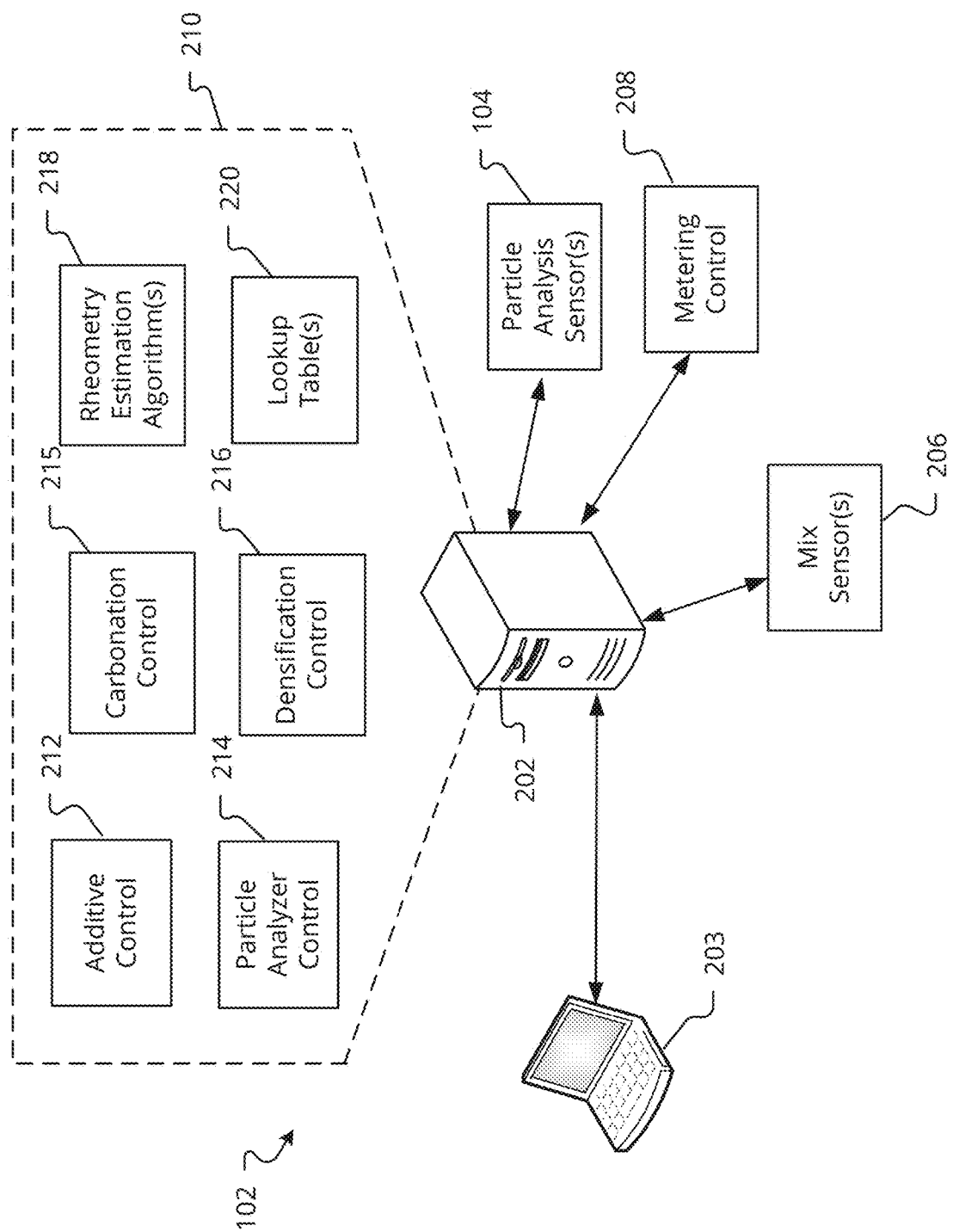
FIG. 2 depicts a block diagram of an exemplary control system for the recycled concrete preparation system of FIG. 1.

FIG. 2 is a block diagram of an exemplary control system 102 for the recycled concrete preparation system 100. In some implementations, control system 102 can control a combined system that recycles concrete and prepares a new concrete mixture using the upgraded concrete particles 130. The system 102 includes a computing system 202 in communication with the concrete mix sensors, particle analysis sensors 104, and a metering control system 208 which can control the control signals 124 for additives. Computing system 202 is configured to control various aspects of the recycled concrete preparation process. For example, computing system 202 can store and execute one or more computer instruction sets to control the execution of aspects of the recycled concrete preparation processes described herein. Computing system 202 can include a system of one or more computing devices. The computing devices can be, e.g., a system of one more servers. For example, a first server can be configured to receive and process data from the concrete mix sensors and the particle analysis sensors 104. Another server can be configured to interface with the metering control system 208 and issue control commands based on analysis results from the first server.

In some implementations, the computing system 202 can be operated or controlled from a user computing device 203. User computing device 203 can be a computing device, e.g., desktop computer, laptop computer, tablet computer, or other portable or stationary computing device.

Briefly, computing system 202 can control the overall recycled concrete preparation system 100 to prepare concrete mixtures. The computing system 202 can use the particle analysis sensors 104 to characterize concrete particles as they are added to a concrete mixture.

In some implementations, the computing system 202 obtains rheometry measurements of a concrete mixture to which the upgraded particles 130 have been added from the mix sensors 206. The system compares the rheometry measurements with estimated rheometry measurements to determine, e.g., whether the concrete mixture will meet desired post-curing mechanical properties or whether additional or additives should be added to the particles.

In some implementations, computing system 202 can include a set of operations modules 210 for controlling different aspects of a concrete recycling and concrete mixture preparation process. In some implementations, the processes of concrete recycling and concrete mixture preparation are performed by separate systems. The operation modules 210 can be provided as one or more computer executable software modules, hardware modules, or a combination thereof. For example, one or more of the operation modules 210 can be implemented as blocks of software code with instructions that cause one or more processors of the computing system 202 to execute operations described herein. In addition or alternatively, one or more of the operations modules can be implemented in electronic circuitry such as, e.g., programmable logic circuits, field programmable logic arrays (FPGA), or application specific integrated circuits (ASIC). The operation modules 210 can include an additive controller 212, a particle analyzer controller 214, carbonation controller 215, densification controller 216, rheometry estimation algorithms 218, rheometry measurement algorithms 218, and one or more lookup tables 220.

Additive controller 212 interfaces with the metering control system 208 to control the addition of additives to the concrete carbonation system 115 and densification system 116. For example, the additive controller 212 can issue commands from the computing system 202 to the metering control system 208 to control the addition of additives to the particles 105 in the carbonation system 115, the densification system 116, or both.

Particle analyzer control 214 interfaces with the particle analysis sensors 104 of the sensors 104. Particle analyzer controller 214 receives and buffers data from the particle analysis sensors 104. The particle analyzer controller 214 can process the sensor data to determine particle characteristics of each analyzed particle. For example, as discussed in more detail below, the particle analyzer controller 214 can execute data analysis algorithms to interpret the sensor data and determine particle characteristics including, but not limited to, particle size distributions, particle shape distributions, and particle surface area distributions.

Carbonation controller 215 determines carbonation process parameters and can interface with the metering control 208 to control the amount of $CO_2$ and $H_2O$ used during the carbonation process. For example, the carbonation controller 215 can estimate the amount of $CO_2$ and/or $H_2O$ to use in a carbonation process based on particle characteristic data received from the particle analyzer control 214. The carbonation controller 215 can then interface with the metering controller 208 to operate valves and from $CO_2$ and/or $H_2O$ supply tanks in order to apply appropriate amounts of $CO_2$ and/or $H_2O$ to the carbonation system 115.

For example, in some implementations, carbonation controller 215 can use a lookup table 220 of experimental data to correlate measured particle characteristics (e.g., size/shape distributions) to experimentally determined carbonation process parameters. For example, the carbonation controller 215 can compare the measured particle characteristics to entries in the lookup table and estimate the carbonation process parameters based on correlating entries of experimentally determined carbonation process parameters in the lookup table. In some examples, the carbonation controller 215 may interpolate between entries in the lookup table 220 or extrapolate the table data when the measured particle characteristics do not precisely match with a table entry.

In some implementations, the carbonation controller 215 can include a machine learning model to estimate the amount of $CO_2$ and/or $H_2O$ to use in a carbonation process from measured particle characteristics. For example, the machine learning model can include a model that has been trained on experimental data to receive particle characteristics of concrete particles as input, and to generate a predicted output, e.g., an estimate the amount of $CO_2$ and/or $H_2O$ to use in in a carbonation system 115. The output can include, but is not limited to, respective amounts (e.g., volumes) of $CO_2$ and/or $H_2O$ to supply to a carbonation system 115 for a batch process, respective flow rates of $CO_2$ and/or $H_2O$ to supply to a carbonation system 115 for a continuous carbonation process, adjustments to carbonation process parameters (e.g., amount or flow rates of $CO_2$ and/or $H_2O$) for iterative processes, or a combination thereof. In some implementations, the machine learning model is a deep learning model that employs multiple layers of models to generate an output for a received input. A deep neural network is a deep machine learning model that includes an output layer and one or more hidden layers that each applies a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model is an ensemble of models that may include all or a subset of the architectures described above.

A machine learning model can be trained to estimate carbonation parameters for carbonating recycled concrete particles based on measured characteristics of the particles. In some examples, the machine learning model can be trained on experimentally determined data relating known characteristics of concrete particles to experimentally determined carbonation parameters.

Densification controller 216 determines carbonation process parameters and can interface with the metering control 208 to control the amount and type of additives to add for a densification process for carbonated particles. Additives can include, but are not limited to, an amount of silicate sources and/or catalysts. For example, the densification controller 216 can estimate the amount and type of additives to add to use in a densification process based on particle characteristic data of carbonated particles received from the particle analyzer control 214. The densification controller 216 can then interface with the metering controller 208 to operate chemical addition systems in order to apply appropriate amounts and types of additives 114 to the carbonation system 116.

For example, in some implementations, densification controller 216 can use a lookup table 220 of experimental data to correlate measured carbonated particle characteristics (e.g., size/shape distributions) to experimentally determined densification process parameters. For example, the densification controller 216 can compare the measured carbonated particle characteristics to entries in the lookup table and estimate the densification process parameters based on correlating entries of experimentally determined carbonation process parameters in the lookup table 220. In some examples, the carbonation controller 215 may interpolate between entries in the lookup table 220 or extrapolate the table data when the measured particle characteristics do not precisely match with a table entry.

In some implementations, the densification controller 216 can include a machine learning model to estimate the amount and type of additives to use in a carbonation process from measured carbonated particle characteristics. For example, the machine learning model can include a model that has been trained on experimental data to receive particle characteristics of carbonated concrete particles as input, and to generate a predicted output, e.g., an estimate the type(s) and amount(s) of additives 114 to use in in a densification system 116. The output can include, but is not limited to, respective amounts (e.g., volumes) of additives to supply to a densification system 116 for a batch process, respective flow or addition rates of additives 114 to supply to a densification system 116 for a continuous densification process, adjustments to densification process parameters (e.g., amounts, types, or flow/addition rates of additives 114) for iterative processes, or a combination thereof. In some implementations, the machine learning model is a deep learning model that employs multiple layers of models to generate an output for a received input. A deep neural network is a deep machine learning model that includes an output layer and one or more hidden layers that each applies a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model is an ensemble of models that may include all or a subset of the architectures described above. A machine learning model can be trained to estimate densification parameters for carbonated concrete particles based on measured characteristics of the particles. In some examples, the machine learning model can be trained on experimentally determined data relating known characteristics of carbonated concrete particles to experimentally determined densification parameters.

In some implementations, the control system can employ rheometry estimation algorithms 218 to estimate the rheometry parameters of a given concrete mixture based on the particle characteristics of the particles. For example, the rheometry estimation algorithms 218 can employ lookup tables 220 to determine estimated rheometry measurements. The computing system can include a lookup table 220 that correlates concrete particle characteristics to experimentally determined rheometry parameters. In some implementations, the rheometry estimation algorithms 218 include algorithms that estimate particle packing efficiencies from the particle parameters and a lookup table 220 that correlates particle packing efficiencies with experimentally determined rheometry parameters. The computing system 202 can then compare the estimated particle packing efficiencies to the data in the lookup table 220 to estimate the rheometry parameters of the concrete mixture.

In some implementations, rheometry estimation algorithms 218 include a packing efficiency model to determine a packing efficiency of the mixture based on the particle characteristics. The model can be a theoretical and analytical particle packing model-based Bayesian optimization algorithm—or other machine learning model—to determine a packing efficiency of the particles and estimate rheometry parameters of the mixture.

In some implementations, the rheometry estimation algorithms 218 can include a machine learning model to estimate particle packing efficiency and/or rheometry parameters for a concrete mixture from measured particle characteristics. For example, the machine learning model can include a model that has been trained on experimental data to receive particle characteristics of concrete particles as input, and to generate a predicted output, e.g., an estimate of the particle packing efficiency, an estimate of rheometry parameters for a concrete mixture, or both. In some implementations, the machine learning model is a deep learning model that employs multiple layers of models to generate an output for a received input. A deep neural network is a deep machine learning model that includes an output layer and one or more hidden layers that each applies a non-linear transformation to a received input to generate an output. In some cases, the neural network may be a recurrent neural network. A recurrent neural network is a neural network that receives an input sequence and generates an output sequence from the input sequence. In particular, a recurrent neural network uses some or all of the internal state of the network after processing a previous input in the input sequence to generate an output from the current input in the input sequence. In some other implementations, the machine learning model is a convolutional neural network. In some implementations, the machine learning model is an ensemble of models that may include all or a subset of the architectures described above.

A machine learning model can be trained to estimate rheometry parameters for concrete mixtures based on measured characteristics of the particles to the mixture. In some examples, the machine learning model can be trained on experimentally determined data relating known characteristics of concrete particles to experimentally determined rheometry parameters.

In some implementations, any of the machine learning models described above can be a feedforward autoencoder neural network. For example, the machine learning model can be a three-layer autoencoder neural network. The machine learning model may include an input layer, a hidden layer, and an output layer. In some implementations, the neural network has no recurrent connections between layers. Each layer of the neural network may be fully connected to the next, there may be no pruning between the layers. The neural network may include an ADAM optimizer, or any other multi-dimensional optimizer, for training the network and computing updated layer weights. In some implementations, the neural network may apply a mathematical transformation, such as a convolutional transformation, to input data prior to feeding the input data to the network.

In some implementations, the machine learning model(s) can be a supervised model. For example, for each input provided to the model during training, the machine learning model can be instructed as to what the correct output should be. The machine learning model can use batch training, training on a subset of examples before each adjustment, instead of the entire available set of examples. This may improve the efficiency of training the model and may improve the generalizability of the model. The machine learning model may use folded cross-validation. For example, some fraction (the "fold") of the data available for training can be left out of training and used in a later testing phase to confirm how well the model generalizes. In some implementations, the machine learning model may be an unsupervised model. For example, the model may adjust itself based on mathematical distances between examples rather than based on feedback on its performance.

The computing system 202 can store one or more lookup tables 220 that correlate different measured parameters to experimentally determined characteristics. For example, the lookup tables 220 can relate measured concrete particle characteristics to carbonation parameters, measured carbonated concrete particle characteristics to densification parameters, and/or measured parameters of a concrete mixture to post-curing concrete properties. For example, the lookup tables 220 can include one or more of: a table correlating desired post-curing concrete characteristics to concrete mixture rheometry parameters, a table correlating particle characteristics to particle packing efficiencies, and a table correlating particle characteristics to mixture remoter parameters. Each lookup table can be a multi-dimensional data structure containing measurable concrete parameters, concrete mixture parameters, or particle characteristics to experimentally determined parameters.

Figure 3:
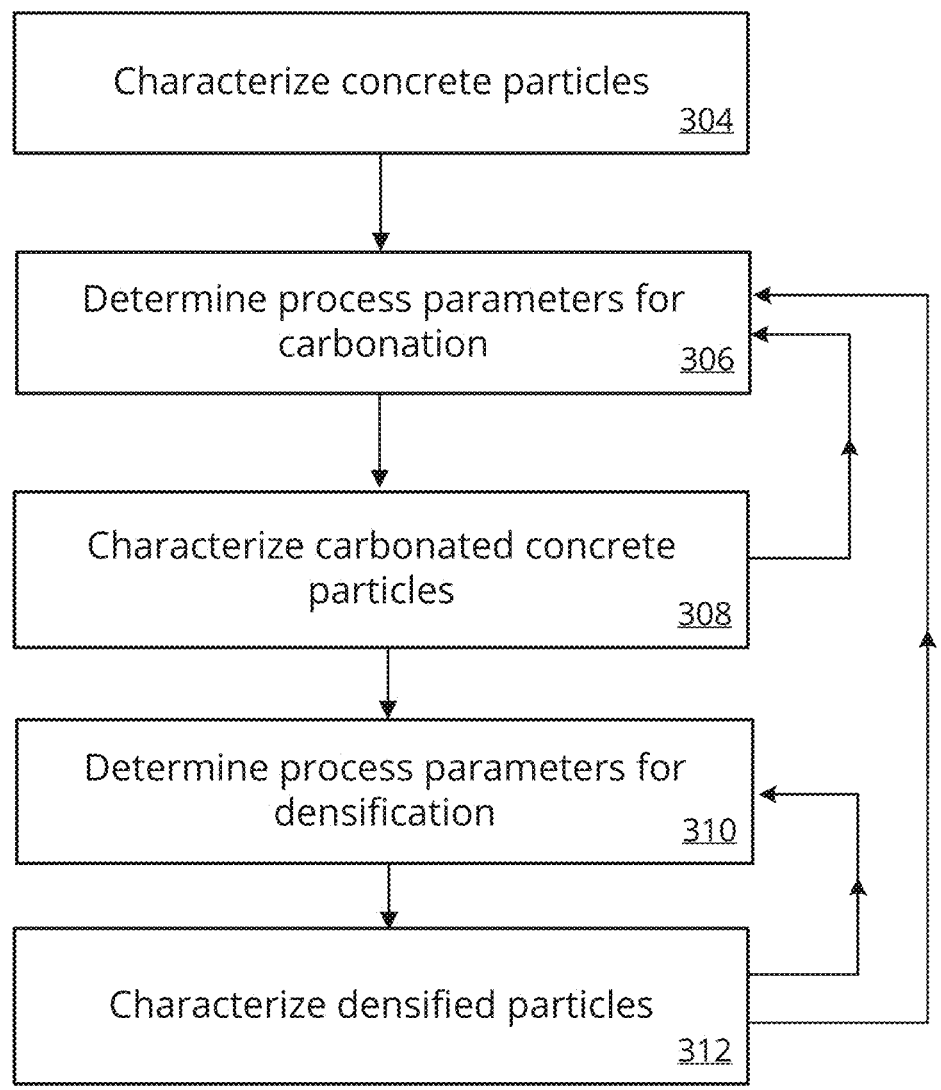
FIG. 3 depicts a flow diagram that illustrates an example process for operating the recycled concrete preparation system of FIG. 1.

FIG. 3 is a flow diagram that illustrates a process 300 for controlling operation of a recycled concrete preparation system 100. The process 300 can be performed by one or more computing devices. For example, as discussed above, the process 300 may be performed by computing system 202 of FIG. 2. For convenience, operations of process 300 are described as being performed by a control system. However, as noted above, some or all of the operations may be performed by various operation modules of an additive manufacturing control system.

The control system characterizes concrete particles (304). For example, the control system can obtain measurement data from a particle analyzing system as the particles are conveyed to a carbonation system or densification system. As discussed above, the control system can receive data from various particle sensors of the particle analyzing system. The control system can analyze the sensor data to characterize the particles. For example, the control system can use image analysis algorithms to detect general shapes and sizes of particles as they are conveyed through a chute or on a conveyor belt.

The control system can estimate a distribution of the various shapes and sizes of the aggregate particles. For example, the control system can characterize particles (e.g., an aggregate) by developing a histogram of the particle size distribution within the aggregate and a histogram of particle shape distribution within the aggregate. The control system can employ the image analysis algorithm to obtain a rough count of aggregate particles within each of a series of size ranges (e.g., >2 mm, 2 mm-3 mm, 3 mm-4 mm, 4 mm-5 mm, etc.). In some implementations, the control system can similarly employ the image analysis algorithm to obtain a rough count of aggregate particles with various shapes or degrees of sphericity. In some implementations, the computing system can characterize the particles by both size and shape distribution.

The control system determines process parameters for carbonation (306). For example, the control system can use the particle characteristics of the ingredients to determine an amount of $CO_2$ and/or $H_2O$ to use in a carbonation process.

In some implementations, the control system can use a lookup table of experimental data to correlate measured particle characteristics (e.g., size/shape distributions) to experimentally determined carbonation process parameters. For example, the computing system can compare the measured particle characteristics to entries in the lookup table and estimate the carbonation process parameters based on correlating entries of experimentally determined carbonation process parameters in the lookup table. In some examples, the control system may interpolate between entries in the lookup table or extrapolate the table data when the measured particle characteristics do not precisely match with a table entry.

In some implementations, the control system includes a machine learning model that is trained using the experimentally determined correlations between particle size characteristics and carbonation process parameters. In such implementations, the control system can provide the particle characteristics to the trained machine learning model as input data vectors. The machine learning model may correlate the input particle characteristics with optimized carbonation process parameters and output the optimized carbonation process parameters.

The control system characterizes the carbonated concrete particles (308). For example, the control system can obtain measurement data from a particle analyzing system as the particles are conveyed to the densification system. As discussed above, the control system can receive data from various particle sensors of the particle analyzing system. The control system can analyze the sensor data to characterize the particles. For example, the control system can use image analysis algorithms to detect general shapes and sizes of particles as they are conveyed through a chute or on a conveyor belt.

In some implementations, characteristics of the carbonated concrete particles can be compared with target characteristics. If the estimated characteristics differ by a threshold amount from the target characteristics, the control system can adjust process conditions for the carbonation system.

The control system determines process parameters for densification (310). For example, the control system can use the particle characteristics of the ingredients to determine an amount of silicate sources and/or catalysts to use in a densification process.

In some implementations, the control system can use a lookup table of experimental data to correlate measured particle characteristics (e.g., size/shape distributions) to experimentally determined densification process parameters. For example, the computing system can compare the measured particle characteristics to entries in the lookup table and estimate the densification process parameters based on correlating entries of experimentally determined densification process parameters in the lookup table. In some examples, the control system may interpolate between entries in the lookup table or extrapolate the table data when the measured particle characteristics do not precisely match with a table entry.

In some implementations, the control system includes a machine learning model that is trained using the experimentally determined correlations between particle size characteristics and densification process parameters. In such implementations, the control system can provide the particle characteristics to the trained machine learning model as input data vectors. The machine learning model may correlate the input particle characteristics with optimized densification process parameters and output the optimized densification process parameters.

The control system characterizes the densified concrete particles (312). For example, the control system can obtain measurement data from a particle analyzing system as the particles are conveyed to a concrete mixing system. As discussed above, the control system can receive data from various particle sensors of the particle analyzing system. The control system can analyze the sensor data to characterize the particles. For example, the control system can use image analysis algorithms to detect general shapes and sizes of particles as they are conveyed through a chute or on a conveyor belt.

In some implementations, characteristics of the densified concrete particles can be compared with target characteristics. If the estimated characteristics differ by a threshold amount from the target characteristics, the control system can adjust process conditions for the densification system, the carbonation system, or both.

Figure 4:
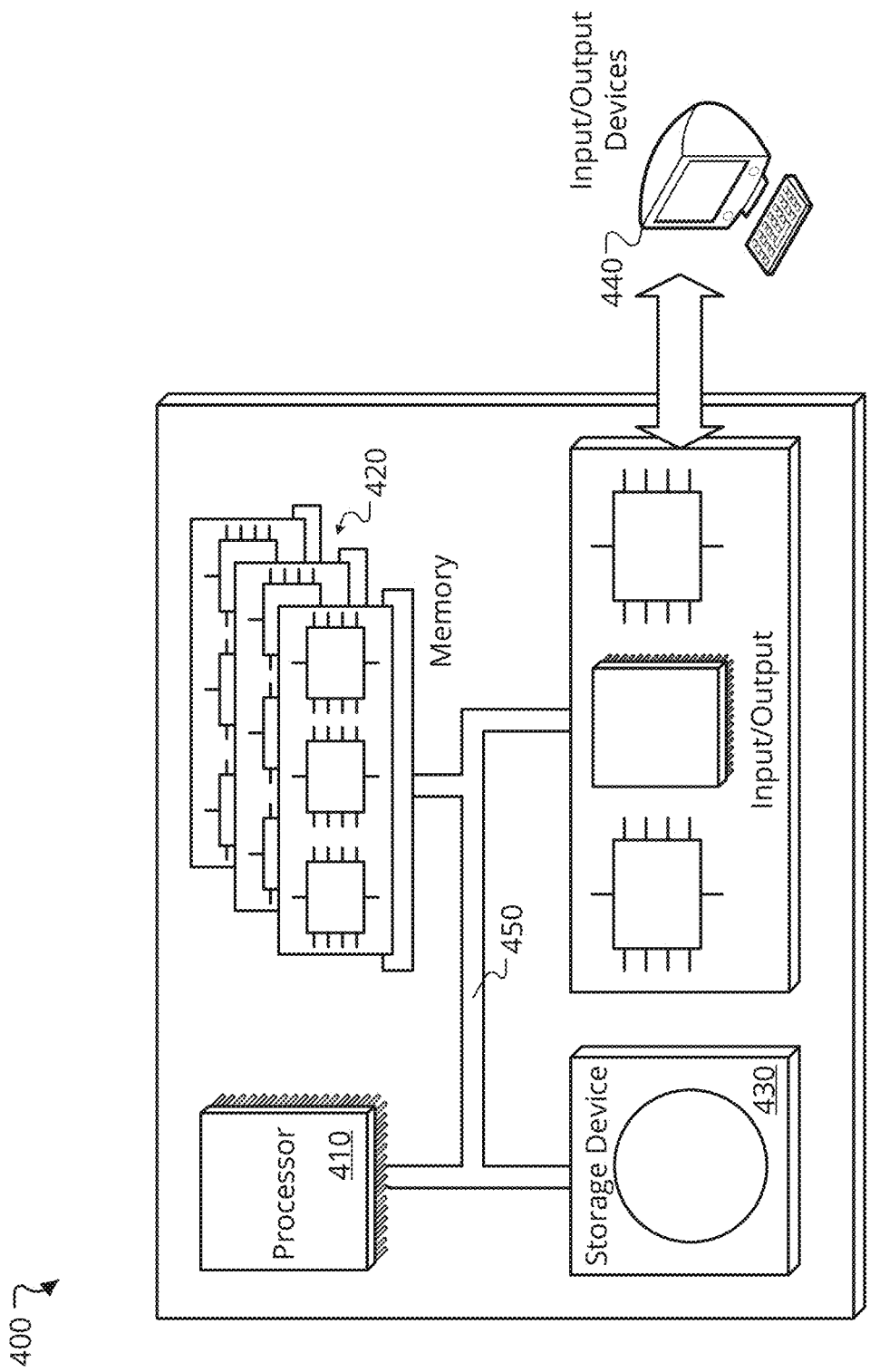
FIG. 4 depicts a schematic diagram of a computer system that may be applied to any of the computer-implemented methods and other techniques described herein.

FIG. 4 is a schematic diagram of a computer system 400. The system 400 can be used to carry out the operations described in association with any of the computer-implemented methods described previously, according to some implementations. In some implementations, computing systems and devices and the functional operations described in this specification can be implemented in digital electronic circuitry, in tangibly-embodied computer software or firmware, in computer hardware, including the structures disclosed in this specification (e.g., system 400) and their structural equivalents, or in combinations of one or more of them. The system 400 is intended to include various forms of digital computers, such as laptops, desktops, workstations, personal digital assistants, servers, blade servers, mainframes, and other appropriate computers, including vehicles installed on base units or pod units of modular vehicles. The system 400 can also include mobile devices, such as personal digital assistants, cellular telephones, smartphones, and other similar computing devices. Additionally, the system can include portable storage media, such as, Universal Serial Bus (USB) flash drives. For example, the USB flash drives may store operating systems and other applications. The USB flash drives can include input/output components, such as a wireless transducer or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) monitor for displaying information to the user and a keyboard and a pointing device such as a mouse or a trackball by which the user can provide input to the computer. Additionally, such activities can be implemented via touch-screen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

As used herein, the term "ready mix" refers to concrete that is batched for delivery from a central plant instead of being mixed on a job site. Typically, a batch of ready mix is tailor-made according to the specifics of a particular construction project and delivered in a plastic condition, usually in cylindrical trucks often referred to as "concrete mixers."

As used herein, the term "real-time" refers to transmitting or processing data without intentional delay given the processing limitations of a system, the time required to accurately obtain data, and the rate of change of the data. Although there may be some actual delays, the delays are generally imperceptible to a user.

While this specification contains many specific implementation details, these should not be construed as limitations on the scope of what is being claimed, which is defined by the claims themselves, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Although the disclosed inventive concepts include those defined in the attached claims, it should be understood that the inventive concepts can also be defined in accordance with the following embodiments.

In addition to the embodiments of the attached claims and the embodiments described above, the following numbered embodiments are also innovative.

Embodiment 1 is a method preparing recycled concrete aggregate (RCA), the method comprising: obtaining, from first optical sensors, first optical measurements of RCA particles as the RCA particles are conveyed past the first optical sensors; determining, based on the first measurements, an initial characterization of the RCA particles; iteratively performing a carbonation process on the RCA particles, obtaining second optical measurements of the RCA particles, and determining, from the second measurements, a second characterization of the RCA particles, wherein conditions of the carbonation process are initially set based on the initial characterization, and the conditions of the carbonation process are adjusted based on the second characterization; ceasing the iterative performance of the carbonation process in response to the second characterization meeting target carbonation characteristics; iteratively performing a densification process on the RCA particles, obtaining third optical measurements of the RCA particles, and determining, from the third measurements, a third characterization of the RCA particles, wherein conditions of the densification process are initially set based on the initial characterization or the second characterization, and the conditions of the densification process are adjusted based on the third characterization; and ceasing the iterative performance of the densification process in response to the third characterization meeting target densification characteristics.

Embodiment 2 is the method of embodiment 1, wherein the carbonation process comprises incubating the RCA particles in a concentration of carbon dioxide gas to promote absorption of carbon dioxide through reaction with calcium hydroxide and water within the RCA particles.

Embodiment 3 is the method of embodiment 2, wherein the conditions of the carbonation process include at least one of a concentration of carbon dioxide gas, an amount of water vapor, and a temperature used for the carbonation process.

Embodiment 4 is the method of any one of embodiments 1 through 3, wherein the densification process comprises reacting the RCA particles with one or more silicates to strengthen the RCA by filling pores within the RCA particles.

Embodiment 5 is the method of embodiment 4, wherein the conditions of the densification process include at least one of an amount of silica, a type of silica, an amount of catalyst, and a type of catalyst used for the densification process.

Embodiment 6 is the method of any one of embodiments 1 through 5, wherein the first optical measurements comprise near infrared (NIR) measurements of at least one of particle size, shape, porosity, or density, and wherein determining the initial characterization comprising applying a regression model to correlate the first optical measurements to reactant content in the RCA particles.

Embodiment 7 is the method of embodiment 6, wherein the reactant content comprises a content of calcium in the RCA particles.

Embodiment 8 is the method of any one of embodiments 1 through 7, further comprising: obtaining final optical measurements of the RCA particles; and determining, based on the final optical measurements, final characteristics of the RCA particles, the final characterization comprising at least one of a geometry or a compressive strength of the RCA particles.

Embodiment 9 is the method of embodiment 8, further comprising: controlling an ingredient metering system to measure and add the RCA particles to concrete mixture based on the final characterization; determining, based on the final characterization, an estimated rheometry measurement of for the concrete mixture by: obtaining an actual rheometry measurement of the concrete mixture; and selectively controlling the ingredient metering system to add more RCA particles or additional ingredients to the concrete mixture based on a comparison of the estimated rheometry measurement with the actual rheometry measurement.

Embodiment 10 is the method of embodiment 9, wherein characteristics of at least one of the additional ingredients comprises one or more of a particle size distribution, a particle shape distribution, or particle sphericity.

Embodiment 11 is the method of embodiment 10, wherein determining an estimated rheometry measurement of the concrete mixture comprises determining, based on the characteristics, a particle packing efficiency for the at least one ingredient, and determining the estimated rheometry measurement based at least in part on the particle packing efficiency.

Embodiment 12 is the method of embodiment 11, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

Embodiment 13 is the method of any one of embodiments 11 through 12, wherein determining the particle packing efficiency comprises applying characteristics as input to a Bayesian optimization algorithm.

Embodiment 14 is the method of any one of embodiments 9 through 13, further comprising: iteratively adjusting the concrete mixture until a stop condition is achieved, wherein each iteration comprises: obtaining rheometry measurements of the concrete mixture; determining, based on the rheometry measurements, whether the concrete mixture satisfies the stop condition; in response to the rheometry measurements not satisfying the stop condition: determining additional portions for one or more of the ingredients to be added to the concrete mixture in order to meet a set of target concrete characteristics, and controlling the ingredient metering system to measure and add the additional portions to the concrete mixture; and in response to determining that the concrete mixture satisfies the stop condition, ceasing the iteratively adjusting the concrete mixture.

Embodiment 15 is the method of embodiment 14, wherein the stop condition is the set of target concrete characteristics.

Embodiment 16 is the method of any one of embodiments 14 through 15, wherein determining whether the concrete mixture satisfies the stop condition comprises determining whether the rheometry measurements indicate that the concrete mixture is likely to achieve at least one of the set of target concrete characteristics within a threshold value.

Embodiment 17 is the method of embodiment 16, wherein determining whether the rheometry measurements indicate that the concrete mixture is likely to achieve at least one of the set of target concrete characteristics comprises: determining target rheometry parameters based on a multi-dimensional lookup table associating experimentally obtained post-curing characteristics to concrete mixtures with known rheological properties; and comparing the rheometry measurements to the target rheometry parameters.

Embodiment 18 is a system comprising: one or more computers and one or more storage devices storing instructions that are operable, when executed by the one or more computers, to cause the one or more computers to perform the method of any one of claims 1 to 17.

Embodiment 19 is a computer storage medium encoded with a computer program, the program comprising instructions that are operable, when executed by data processing apparatus, to cause the data processing apparatus to perform the method of any one of claims 1 to 17.

The invention claimed is:

1. A method of preparing recycled concrete aggregate (RCA), the method comprising:
obtaining, from first optical sensors, first optical measurements of RCA particles as the RCA particles are conveyed past the first optical sensors;
determining, based on the first optical measurements, an initial characterization of the RCA particles;
iteratively performing a carbonation process on the RCA particles to obtain carbonated RCA particles, after each iteration:
obtaining second optical measurements of the carbonated RCA particles, and
determining, from the second optical measurements, a second characterization of the RCA particles, wherein conditions of the carbonation process are initially set based on the initial characterization, and the conditions of the carbonation process, for subsequent iterations, are adjusted based on the second characterization;
ceasing the iterative performance of the carbonation process in response to the second characterization meeting target carbonation characteristics;
iteratively performing a densification process on the carbonated RCA particles to obtain upgraded-carbonated RCA particles, after each iteration:
obtaining third optical measurements of the upgraded-carbonated RCA particles, and
determining, from the third optical measurements, a third characterization of the RCA particles, wherein conditions of the densification process are initially set based on the initial characterization or the second characterization, and the conditions of the densification process, for subsequent iterations, are adjusted based on the third characterization; and
ceasing the iterative performance of the densification process in response to the third characterization meeting target densification characteristics.

2. The method of claim 1, wherein the carbonation process comprises incubating the RCA particles in a concentration of carbon dioxide gas to promote absorption of carbon dioxide through reaction with calcium hydroxide and water within the RCA particles.

3. The method of claim 2, wherein the conditions of the carbonation process include at least one of a concentration of carbon dioxide gas, an amount of water vapor, and a temperature used for the carbonation process.

4. The method of claim 1, wherein the densification process comprises reacting the carbonated RCA particles with one or more silicates to strengthen the carbonated RCA by filling pores within the RCA particles, thereby, yielding upgraded-carbonated RCA particles.

5. The method of claim 4, wherein the conditions of the densification process include at least one of an amount of silica, a type of silica, an amount of catalyst, and a type of catalyst used for the densification process.

6. The method of claim 1, wherein the first optical measurements comprise near infrared (NIR) measurements of at least one of particle size, shape, porosity, or density, and wherein determining the initial characterization comprising applying a regression model to correlate the first optical measurements to reactant content in the RCA particles.

7. The method of claim 6, wherein the reactant content comprises a content of calcium in the RCA particles.

8. The method of claim 1, further comprising:
obtaining final optical measurements of the upgraded-carbonated RCA particles; and
determining, based on the final optical measurements, final characteristics of the upgraded-carbonated RCA particles, the final characterization comprising at least one of a geometry or a compressive strength of the RCA particles.

9. The method of claim 8 further comprising:
controlling an ingredient metering system to measure and add the upgraded-carbonated RCA particles to concrete mixture based on the final characterization;
determining, based on the final characterization, an estimated rheometry measurement of for the concrete mixture by:
obtaining an actual rheometry measurement of the concrete mixture; and
selectively controlling the ingredient metering system to add more upgraded-carbonated RCA particles or additional ingredients to the concrete mixture based on a comparison of the estimated rheometry measurement with the actual rheometry measurement.

10. The method of claim 9, wherein characteristics of at least one of the additional ingredients comprises one or more of a particle size distribution, a particle shape distribution, or particle sphericity.

11. The method of claim 10, wherein determining an estimated rheometry measurement of the concrete mixture comprises determining, based on the characteristics, a particle packing efficiency for the at least one ingredient, and determining the estimated rheometry measurement based at least in part on the particle packing efficiency.

12. The method of claim 11, wherein determining the estimated rheometry measurement based at least in part on the particle packing efficiency comprises comparing the particle packing efficiency to a multi-dimensional lookup table that associates particle packing efficiencies to experimentally determined expected rheometry measurements.

13. The method of claim 11, wherein determining the particle packing efficiency comprises applying characteristics as input to a Bayesian optimization algorithm.

14. The method of claim 9, further comprising:
iteratively adjusting the concrete mixture until a stop condition is achieved, wherein each iteration comprises:
obtaining rheometry measurements of the concrete mixture;
determining, based on the rheometry measurements, whether the concrete mixture satisfies the stop condition;
in response to the rheometry measurements not satisfying the stop condition:
determining additional portions for one or more of the ingredients to be added to the concrete mixture in order to meet a set of target concrete characteristics, and
controlling the ingredient metering system to measure and add the additional portions to the concrete mixture; and
in response to determining that the concrete mixture satisfies the stop condition, ceasing the iteratively adjusting the concrete mixture.

15. The method of claim 14, wherein the stop condition is the set of target concrete characteristics.

16. The method of claim 14, wherein determining whether the concrete mixture satisfies the stop condition comprises determining whether the rheometry measurements indicate that the concrete mixture is likely to achieve at least one of the set of target concrete characteristics within a threshold value.

17. The method of claim 16, wherein determining whether the rheometry measurements indicate that the concrete mixture is likely to achieve at least one of the set of target concrete characteristics comprises:
determining target rheometry parameters based on a multi-dimensional lookup table associating experimentally obtained post-curing characteristics to concrete mixtures with known rheological properties; and
comparing the rheometry measurements to the target rheometry parameters.

18. A recycled concrete aggregate (RCA) preparation system comprising:
a plurality of optical sensors arranged within the system to measure attributes of crushed RCA at different process stages;
a carbonation sub-system;
a densification sub-system;
at least one processor in communication with the plurality of optical sensors, the carbonation sub-system, and the densification sub-system; and
a data store coupled to the at least one processor having instructions stored thereon which, when executed by the at least one processor, causes the at least one processor to perform operations comprising:
obtaining, from first optical sensors, first optical measurements of RCA particles as the RCA particles are conveyed past the first optical sensors;
determining, based on the first optical measurements, an initial characterization of the RCA particles;
iteratively performing a carbonation process on the RCA particles to obtain carbonated RCA particles, after each iteration:
obtaining second optical measurements of the carbonated RCA particles, and
determining, from the second optical measurements, a second characterization of the RCA particles, wherein conditions of the carbonation process are initially set based on the initial characterization, and the carbonation sub-system is controlled to adjust conditions of the carbonation process, for subsequent iterations, based on the second characterization;
ceasing the iterative performance of the carbonation process in response to the second characterization meeting target carbonation characteristics;
iteratively performing a densification process on the carbonated RCA particles to obtain upgraded-carbonated RCA particles, after each iteration:
obtaining third optical measurements of the upgraded-carbonated RCA particles, and
determining, from the third optical measurements, a third characterization of the RCA particles, wherein conditions of the densification process are initially set based on the initial characterization or the second characterization, and the densification sub-system is controlled to adjust conditions of the densification process, for subsequent iterations, based on the third characterization; and ceasing the iterative performance of the densification process in response to the third characterization meeting target densification characteristics.

19. The system of claim 18, wherein the carbonation process comprises incubating the RCA particles in a concentration of carbon dioxide gas to promote absorption of carbon dioxide through reaction with calcium hydroxide and water within the RCA particles, wherein the conditions of the carbonation process include at least one of a concentration of carbon dioxide gas, an amount of water vapor, and a temperature used for the carbonation process, wherein the densification process comprises reacting the carbonated RCA particles with one or more silicates to strengthen the carbonated RCA by filling pores within the RCA particles, thereby, yielding upgraded-carbonated RCA particles, and wherein the conditions of the densification process include at least one of an amount of silica, a type of silica, an amount of catalyst, and a type of catalyst used for the densification process.

20. A non-transitory computer readable storage medium storing instructions that, when executed by at least one processor, cause the at least one processor to perform operations comprising:

obtaining, from first optical sensors, first optical measurements of RCA particles as the RCA particles are conveyed past the first optical sensors;

determining, based on the first optical measurements, an initial characterization of the RCA particles;

iteratively performing a carbonation process on the RCA particles to obtain carbonated RCA particles, after each iteration:

obtaining second optical measurements of the carbonated RCA particles, and determining, from the second optical measurements, a second characterization of the RCA particles, wherein conditions of the carbonation process are initially set based on the initial characterization, and the conditions of the carbonation process, for subsequent iterations, are adjusted based on the second characterization;

ceasing the iterative performance of the carbonation process in response to the second characterization meeting target carbonation characteristics;

iteratively performing a densification process on the carbonated RCA particles to obtain upgraded-carbonated RCA particles, after each iteration:

obtaining third optical measurements of the upgraded-carbonated RCA particles, and determining, from the third optical measurements, a third characterization of the RCA particles, wherein conditions of the densification process are initially set based on the initial characterization or the second characterization, and the conditions of the densification process, for subsequent iterations, are adjusted based on the third characterization; and ceasing the iterative performance of the densification process in response to the third characterization meeting target densification characteristics.

* * * * *